United States Patent [19]

Phillips

[11] Patent Number: 4,935,223
[45] Date of Patent: Jun. 19, 1990

[54] LABELED CELLS FOR USE IN IMAGING

[75] Inventor: William Phillips, San Antonio, Tex.

[73] Assignee: Board of Regents, The University of Texas System, Austin, Tex.

[21] Appl. No.: 229,069

[22] Filed: Aug. 4, 1988

[51] Int. Cl.$^5$ .................... A61K 49/02; A61K 49/00
[52] U.S. Cl. ......................................... 424/1.1; 424/9
[58] Field of Search ................................. 424/1.1, 9

[56] References Cited

U.S. PATENT DOCUMENTS

| | | | |
|---|---|---|---|
| 3,991,173 | 11/1976 | Sinn et al. | 424/1.1 |
| 4,224,313 | 9/1980 | Zimmerman et al. | 424/1.1 X |
| 4,269,826 | 5/1981 | Zimmerman et al. | 424/1.1 X |
| 4,466,951 | 8/1984 | Pittman | 424/1.1 |
| 4,497,791 | 2/1985 | Gamble et al. | 424/1.1 |

OTHER PUBLICATIONS

U. Zimmermann et al., Enzyme Loading of Electrically Homogeneous Human Red Blood Cell Ghosts Prepared by Dielectric Breakdown, Biochimica et Biophysica Acta, 1976, pp. 460–474.
K. Kinosita et al., Survival of Sucrose-Loaded Erythrocytes in the Circulation, Nature vol. 272, Mar. 16, 1978, pp. 258–260.
Thakur et al., Neutrophil Labeling: Problems and Pitfalls, Seminars in Nuclear Medicine, vol. XIV, No. 2 (Apr.), 1984, pp. 107–117.
McAfee, Subramanian, and Gagne, Technique of Leukocyte Harvesting and Labeling: Problems and Perspectives, Seminars in Nuclear Medicine, vol. XIV, No. 2 (Apr.), 1984, pp. 83–106.
Mrinal K. Dewanjee, Cardiac and Vascular Imaging with Labeled Platelets and Leukocytes, Seminars in Nuclear Medicine, vol. XIV, No. 3 (Jul.), 1984, pp. 154–187.
Moser et al., Imaging of Venous Thromboemboli with Labeled Platelets, Seminars in Nuclear Medicine, vol. XIV, No. 3 (Jul.), 1984, pp. 188–197.
Janice P. Dutcher, Labeled Cells in Patients with Malignancy, Seminars in Nuclear Medicine, vol. XIV, No. 3 (Jul.), 1984, pp. 251–260.
Gordon et al., Autophagic Sequestration of [$^{14}$C]Sucrose Introduced into Isolated Rat Hepatocytes by Electrical and Non-Electrical Methods, Experimental Cells Research 160 (1985), pp. 449–458.
Serpersu et al., Reversible and Irreversible Modification of Erythrocyte Membrane Permeability by Electric Field, Biochimica et Biophysica Acta 812 (1985), pp. 779–785.
Tsong et al., Use of Voltage Pulses for the Pore Opening and Drug Loading, and the Subsequent Resealing of Red Blood Cells, Biblthca haemat., No. 51, (Karger, Basel 1985), pp. 108–114.
Loken et al., Clinical Use of Indium-111 Labeled Blood Products, Clinical Nuclear Medicine, Dec. 1985, vol. 10, No. 12, pp. 902–911.
Milgram, M. D. et al., Human Scanning with In-111 Oxine Labeled Autologous Lymphocytes, pp. 30–34.
Val M. Runge et al., $^{111}$In-Labeled Eosinophils: Localization of Inflammatory Lesions and Parasitic Infections in Mice, Nucl. Med. Biol., vol. 12, No. 2, 1985, pp. 135–144.
Ulrich Zimmerman, Electrical Breakdown, Electropermeabilization and Electrofusion, Rev. Physiol. Biochem. Pharmacol., vol. 105, ©by Springer-Verlag 1986, pp. 176–256.
Josiane Eid et al., Efficient Introduction of Plasmid DNA into *Trypanosoma brucei* and Transcription of a Transfected Chimeric Gene, Proc. Natl. Acad. Sic. USA, vol. 84, Nov. 1987, pp. 7812–7816.
A. M. Peters, Recent Advances in Cell Labellling, Nuclear Medicine Communications 8, (1987), pp. 313–316.
Carl A. K. Borrebaeck, In Vitro Immunization in Hybridoma Technology, Progress in Biotechnology 5, Sep. 1987, pp. 1–26.
H. Liang, et al., Uptake of Fluorescence-Labeled Dextrans by 10T ½ Fibroblasts Following Permeation by Rectangular and Exponential-Decay Electric Field Pulses, BioTechniques, vol. 6, No. 6 (1988), pp. 550–558.
Sergio Grinstein et al., Receptor-Mediated Activation of Electropermeabilized Neutrophils, The Journal of Biological Chemistry, vol. 263, No. 4, Feb. 5, 1988, pp. 1779–1783.

*Primary Examiner*—John S. Maples
*Attorney, Agent, or Firm*—Arnold, White & Durkee

[57] ABSTRACT

A process is provided for the labeling of viable eucaryotic cells. The process includes the steps of collecting, separating, and introducing a quantity of first type cells into a non-toxic media suitable to conduct an electric field. A labeling material is added to this media. The media containing the first type cells and the labeling material is pulsed for a period of time with an electric field, sufficient to render the cell membranes permeable so that the labeling material permeates the cells and becomes trapped therein upon cessation of the pulsing to produce labeled cells. Also provided is a process for diagnostically imaging pathological sites in a patient. This process contains the additional steps of administering the labeled cells to a patient and monitoring the localization of the labeling material in the patient to image the locus of a specific pathosis.

40 Claims, No Drawings

LABELED CELLS FOR USE IN IMAGING

BACKGROUND OF THE INVENTION

The present invention relates to the preparation and use for imaging of radionuclide-labeled cells. In the last ten years, the use of blood cells labeled with radioactive tracers for diagnostic imaging has increased. The references cited in this application are incorporated by reference herein in their entirety related to the context of their citations. Labeled cells are currently being used for an ever increasing variety of applications. Erythrocytes, which are the most frequently used labeled cells, have been successfully labeled with the radioisotope $^{99m}$technetium ($^{99m}$Tc). $^{99m}$Tc-labeled erythrocytes have been used to study cardiac function (MUGA scans) and for the detection and localization of gastrointestinal bleeding. Unfortunately, a successful procedure for labeling other blood cells, e.g., leukocytes and platelets, with $^{99m}$Tc has yet to be established.

Leukocytes and platelets have, however, been successfully labeled with the radioisotope, $^{111}$indium ($^{111}$In) The use of $^{111}$In-labeled leukocytes has gradually increased since their introduction in 1976, and research in this area continues to be very active (Milgran, et al., Clin. Nucl. Med., Vol. 10, pp. 30–34, 1985). In the Milgran article, $^{111}$In-labeled lymphocytes were administered to patients with chronic inflammatory disease. Whole body gamma-ray camera scans were performed in order to image localization of the $^{111}$In-label. Localization of the $^{111}$In-label was normally imaged in the spleen, the liver, bone marrow, and the cervical and inguinal lymph nodes. Localization of the $^{111}$In-label outside of these areas was considered abnormal or positive. Patients with chronic osteomyelitis, chronic arthritic disease, or chronic bladder inflammation had positive scans.

$^{111}$In-labeled eosinophils were also used for the detection and localization of inflammatory lesions and parasitic infections which could not be detected by other diagnostic modalities. (Runge, et al., Nucl. Med. Biol. Vol. 12, No. 2, pp. 135–144, 1985). In The Runge Article, $^{111}$In-labeled eosinophils were used to image the chemotactic response of eosinophils to intradermal injections of soluble schistoscoma antigen, S. mansoni eggs, E.coli, and turpentine. Gamma-ray cameras were used to image the localization of the radiolabel. Soluble schistosoma antigen and s. mansoni eggs provided a greater stimulus for localization than E. coli or turpentine. The article suggested that $^{111}$In-labeled-eosinophil scans were more sensitive to parasitic infections than bacterial infections.

$^{111}$In-labeled leukocytes have been used in the early detection of occult infection. (Loken, et al., Clin. Nucl. Med. Vol. 10, No. 12, pp. 902–911, 1985). In The Loken Article, $^{111}$In-labeled leukocytes were used to assess occult infections in more than 1700 patients. Of the patients determined to have an occult infection, the sensitivity, specificity, and accuracy of the $^{111}$In-labeled leukocyte was determined to be 88%, 96%, and 94%, respectively.

$^{111}$In-labeled lymphocytes have been used to study the disease process in patients with chronic lymphocytic leukemia and well differentiated lymphoma. (Dutcher, Sem. Nucl. Med., Vol. 14, No. 3, 1984). In the Dutcher article, $^{111}$In-labeled lymphocytes were used to study the migration of carcinoma cells, normal lymphoid cells, and malignant lymphoid cells in patients with malignancy. Determining the migration of these cell types was beneficial in helping to understand the disease processes and the mechanism of metastasis.

$^{111}$In-labeled platelets were used for the evaluation of intracoronary thrombolysis and the quantitative estimation of platelet thrombosis on vascular grafts. (Dewanjee, Sem. Nucl. Med. Vol. 14, No. 3, 1984). In the Dewanjee article, $^{111}$In-labeled platelets were used to determine the number of adherent platelets on the deendothelialized surfaces of damaged cell walls and synthetic vascular grafts. Platelet deposition was recorded in denuded tissues, atherosclerotic vessels, and prostheses placed in the circulatory system. $^{111}$In-labeled platelets were also used to determine platelet consumption during open heart surgery. The article additionally described the in vivo evaluation of myocardial infarction using $^{111}$In-labeled leukocytes.

As indicated above, leukocytes and platelets can be successfully labeled with $^{111}$In. The current state of technology for labeling leukocytes with $^{111}$In involves the use of an $^{111}$In-indium oxine complex. The indium oxine portion of the $^{111}$In-indium oxine complex penetrates the cell membrane and carries the $^{111}$In into the cell interior.

One disadvantage of the $^{111}$In-indium oxine labeling method is that it is toxic to leukocytes. Studies have demonstrated decreased chemotaxis and increased leukocyte adherence after $^{111}$In-indium oxine labeling. (Shechan et. al., Inter J. Nucl. Med. Bio. Vol. 12 243–247, 1985; Linhart-Colas et. al., Brit. J. Hem. Vol. 53, pp. 31–34, 1981).

Another disadvantage of the $^{111}$In-indium oxine labeling method is that it is toxic to platelets. Decreased platelet aggregation has been noted after $^{111}$In-indium oxine labeling.

Yet another disadvantage of the $^{111}$In-labeling method is that $^{111}$In is extremely expensive. $^{111}$In is expensive because it is produced by a cyclotron. Therefore, clinical studies using $^{111}$In are often cost-prohibitive.

$^{99m}$Tc, on the other hand, is an ideal imaging agent for labeling leukocytes and platelets. $^{99m}$Tc is the most commonly used radioisotope in nuclear medicine. $^{99m}$Tc is inexpensive ($0.35/mCi) because it is produced by a reactor.

Attempts to label leukocytes and platelets with $^{99m}$Tc have failed. These attempts have resulted in elution (leaking) of the $^{99m}$Tc from the cells. (Thakur, et al., Sem. in Nuc. med. Vol 14(2), 107–117, 1984). A review article published in 1984 noted that "the challenge of developing a $^{99m}$Tc cell-labeling agent comparable to the $^{111}$In lipophillic chelates has still no: been met." (McAfee et al., Sem. in Nucl. Med. Vol. 14(2), p.82–105, 1984). Over the last few years many $^{99m}$Tc agents have been proposed as leukocytes labels but none have enjoyed lasting success. (Peters, Nucl. Med. Comm. 8, 313–316, 1987).

Electroporation (electropermeation) involves the exposure of cells to a pulsed electric field. This electric field causes a dielectric breakdown of the cell membrane forming pores in the cell membrane. These pores allow the transfer of molecules from outside the cell into the cell interior. These pores seal upon the cessation of the electric field. Cells remain viable, and electron micrographic studies show no damage from the electroporation procedure. (Zimmerman, Rev. Physiol. Biochem. pharmacol., Vol. 105, pp. 175–257, 1986).

Electroporation is a technology with many different applications. One application of electroporation is the transfection of DNA into plant and mammalian cells. This technique was first performed in 1982, and since that time there has been much research in this area. (Chu, et. al., Nucl. Acid Res. Vol. 15(3), pp. 1311–1326, 1987; Eid, et. al., Proc. Natl. Acad. Sci. USA Vol. 84, pp. 7812–7816, 1987). In the Eid article, using electroporation, DNA having a molecular weight of four million was transfected into procaryotic cells. In another study using electroporation, molecules having molecular weights of between 9,000 and 154,000 passed through cell membranes. (Liang et al., Biotech. Vol. 6, No. 6, pp. 550–558, 1988). The molecules used by Liang et al. were fluorescently labeled dextrans. The label was used to monitor the extent of incorporation.

Erythrocytes have been labeled with C-14 sucrose by electroporation. (Kinosita et al., Nature vol. 27, pp.258–260, 1978). These labeled erythrocytes were injected into a mouse where they remained in circulation with a normal average half life. There was no apparent elution of the C-14 sucrose from the erythrocytes.

Electroporated cells have been suggested as a new drug delivery system. (Zimmerman et al., Biochimica et. Biophysica. Acta, Vol. 436, pp. 460–474, 1976). In the Zimmerman article, the authors disclose a technique for loading an enzyme, urease, into human red blood cell ghosts (hemoglobin-depleted erythrocytes). In another article, molecules as large as tetrasacharides were loaded into viable erythrocytes (not hemoglobin-depleted ghosts) without affecting cell viability. (Tsong, et al., Biblthca. Haemat., No. 51, pp. 108–114, 1985).

SUMMARY OF THE INVENTION

One aspect of the present invention includes a process for producing labeled living eucaryotic cells for use in imaging. The inventive process includes the steps of collecting an amount of living cells, separating from said amount a plurality of first type cells, introducing a quantity of said first type cells into a non-toxic media, said media also being electrically conductive, adding a labeling material to said media, and pulsing said media for a period of time with an electric field sufficient to render membranes of said first type cell permeable so that said labeling material permeates the cells and becomes trapped therein upon cessation of the pulsing to produce labeled cells.

In another aspect of the present invention a process is provided for diagnostically imaging pathological sites. The inventive process includes the steps of collecting an amount of living cells, separating from said amount a plurality of first type cells, introducing a quantity of said first type cells into a non-toxic media, said media being electrically conductive, introducing a labeling material into said media (before or after the cells), pulsing said media for a period of time with an electric field sufficient to render membranes of said first type cells permeable so that said labeling material permeates the cells. Upon cessation of the pulsing the labeling material becomes entrapped to produce labeled cells. The labeled cells are removed from said media and may be administered to a patient. The localization of the label of said labeled cells in the patient is then monitored to image the locus of a specific pathosis.

DESCRIPTION OF THE PREFERRED EMBODIMENTS

This invention relates to the development of a novel method for labeling eucaryotic cells and using such labeled cells. Specifically, the present invention relates to a process for labeling viable cells, particularly eucaryotic cells using a pulsed electric field sufficient to render cell membranes permeable so that a labeling material permeates the cells. Upon cessation of the pulsing, the labeling material becomes trapped therein to produce labeled cells. The invention further relates to the diagnostic imaging of pathological sites within the body using labeled viable cells produced by the above process.

Electroporation as a labeling technique offers many advantages over the $^{111}$In-indium oxine labeling technique or other prior art labeling techniques. Among these advantages include: (1) labels are incorporated into the cell cytoplasm; (2) cells remain biologically active in vivo after labeling; (3) unlike other prior art labeling techniques, this method, when properly done, is not toxic to cells; (4) viable labeled cells are provided for the imaging of specific organ systems, occult abscesses, occult tumors or inflammatory processes, for example; (5) radionuclides such as $^{99m}$technetium, which are safe, non-toxic to the labeled cell, inexpensive and available may be employed; (6) no significant elution of the labeling agent from the cell ensues; (7) a plurality of labeling agents may be successfully loaded into viable cells for imaging purposes; and (8) a plurality of cell types may be successfully labeled using this method.

In one embodiment the labeling process includes the following steps of: (1) collecting an amount of living cells; (2) separating from said amount a plurality of first type cells; (3) introducing a quantity of said first type cells into a non-toxic media, said media being electrically conductive; (4) adding a labeling material to said media; and (5) pulsing said media with an electric field sufficient to render membranes of said first type cell permeable so that said labeling material permeates the cells and becomes trapped therein upon cessation of the pulsing to produce labeled cells.

One step of the present invention is the collection of an amount of living eucaryotic cells. Generally, the purpose of this step is the collection and preparation of living eucaryotic cells for the later separation and labeling of a specific type of cell.

The cells may be collected in a number of different ways. In one embodiment using standard venipuncture techniques these cells are collected from a human. Such collection may be done, for example, with a standard 18 gauge hypodermic needle. 40–60 ml of whole human blood is drawn into a syringe containing an anticoagulant. The preferred anticoagulant is acid citrate dextrose formula A. 1.6 ml of acid citrate dextrose formula A is added for every 10 ml of whole human blood collected. Acid citrate dextrose formula A is composed of trisodium citrate 22.0 g, citrate acid 8.0 g, dextrose 24.5 g, and enough water to make 1000 ml. In acid citrate dextrose formula A, the citrate chelates calcium serving as an anticoagulant, the dextrose provides a source of energy, and the citrate acid gives the solution a pH of about five. To facilitate the separation of cell types, hydroyxethyl starch is also added to the syringe. 3 ml of hydroyxethyl starch is added for every 10 ml of whole human blood collected.

In an embodiment involving animal testing, using standard venipuncture technique, 20 ml of whole blood are removed from the ear vein of a rabbit. To this blood 500 units of benzyl alcohol-free heparin is added. Benzyl alcohol-free heparin is utilized as an anticoagulant and is prepared by placing 75,000 units of heparin in 1000 ml of 0.9% sodium chloride in water.

Another step in the process is separating from the collected cells a plurality of first type cells. These first type cells may be, for example, any eucaryotic cell type desired for a particular purpose. Preferably, it is a cell type which is included in the whole blood of the animal. More preferably, the first type cells may be, for example, human leukocytes (for example eosinophils) or platelets.

In one embodiment the first type cells are human leukocytes. The leukocytes are separated from whole blood in the following manner. Red blood cells are allowed to sediment at room temperature for 30-60 minutes to produce a leukocyte-rich-plasma. The leukocyte-rich plasma is transferred from the syringe into a polypropylene tube which is centrifuged at 225 x g for 5 minutes. This will pellet the leukocytes. The leukocyte pellet is then gently resuspended in platelet-free plasma. This will make a suspension of leukocytes in plasma.

In another embodiment, platelets are separated from whole blood in the following manner. Whole blood is placed in ten separate 10 ml polypropylene tubes. The tubes are centrifuged at 150 x g for 20 minutes. The supernatant is platelet-rich plasma. The supernatant plasma is removed and placed in six 10 ml polypropylene tubes. The tubes are centrifuged at 880 x g for 10 minutes to pellet the platelets. The platelet pellets are gently resuspended in plasma.

Another step in the present invention is the introduction of a quantity of said first type cells into a non-toxic media which is electrically conductive. Although, any non-cytotoxic electrically conductive media may be used for this process, platelet-poor plasma is preferred. A media including 50% phosphate buffered saline and 50% platelet-poor plasma is more preferably used. These media are preferred because they are isotonic and are non-toxic to eucaryotic cells. These media are also preferred because they may be administered to a subject animal, for example a human, without substantial toxicity.

Still another step is the addition of the labeling material to the media. Although a number of different labeling materials are within the scope of this invention, radioisotopes and paramagnetic agents are preferred labeling materials. More preferably, radioisotopes are utilized as the labeling material of choice. $^{99m}$technetium is a most preferred labeling material.

Any source of pharmaceutically acceptable $^{99m}$technetium agent can be used, and a number of technetium radionuclide generators are available. Preferably, the $^{99m}$technetium agent should be water-soluble, with preferred agents being $^{99m}$technetium pyrophosphate, $^{99m}$technetium glucoheptonate or $^{99m}$technetium methylene diphosphonate. In one embodiment the labeling material is preferably dissolved in saline and is added to the first cell type suspension in a ratio of four parts first type cell suspension to one part labeling agent in saline.

The present invention is not limited to preparations of $^{99m}$Tc. Other radionuclides, such as $^{95m}$Tc $^{123}$I and $^{67}$Ga are also applicable in the labeling process. Depending on the clinical application, compounds labeled with $^{99m}$Tc or $^{99}$Tc are ideal scintigraphic imaging agents; whereas, $^{99}$Tc-labeled substances may find a wide range of applications in in vitro assays. The longer physical half life of $^{95m}$Tc, (61 days), $^{123}$I (13 hours) or Ga (78 hours) provides an added advantage for imaging procedures requiring observation periods of various lengths.

The use of technetium as the preferred labeling material provides an advantage over prior art labeling methods. $^{99m}$Tc is inexpensive, widely available and easily imaged by equipment available in substantially all hospitals and research centers. Furthermore, the embodiments of the present invention which utilize $^{99m}$Tc as the labeling agent are non-toxic to the labeled cell. Accordingly, cells remain viable and there is no elution of the labeling agent.

An electric field pulses the media containing the first cell type and the labeling agent. This pulsing renders the membranes of the first cell type permeable by opening pores in the cell membrane. These pores allow the labeling material to permeate the cell. When the pulsing ceases, the pores close and the labeling material is trapped in the cell. Labeled cells are thereby created.

In one embodiment, media containing both the first type cells and the labeling material is placed in a standard electroporation cuvette. This cuvette is placed in an ice-water bath, preferably for ten minutes at about 4° C. The cuvette is removed from the ice bath and placed in the chamber of a standard electroporation device. The pulse length and field strength parameters of the electroporation device are adjusted according to the cell type and the labeling material to be used. Preferably, the field strength ranges for labeling are no less than about 1.0 kilovolts/cm to no more than about 20 kilovolts/cm, and the pulse length ranges are no less than about 0.01 milliseconds to no greater than about 5.0 milliseconds. The higher field strength ranges may be particularly useful for labeling bacteria (should a use be found for labeled bacteria) or platelets.

The electrical field is pulsed through the media a number of times, depending on pulse length and field strength parameters previously set. Preferably the number of pulses is at least one and no greater than about twenty.

The first cell type/labeling material suspension is removed from the electroporation apparatus and is placed in an ice water bath to reach a temperature of preferably about 4° C. Preferably, the first cell type/labeling material suspension remains in the ice water bath for about no less than about 10 minutes and about no longer than about 60 minutes. The first cell type/labeling material suspension is then placed in an environment which approximates room temperature, preferably in a polypropylene tube for about 10 minutes. The first cell type/labeling material suspension is then placed in a warm water bath, preferably at about 37° C. The first cell type/labeling material suspension preferably remains immersed in the warm water for at least about 30 minutes but no longer than about 60 minutes. This allows resealing of the cell membrane pores, thereby entrapping the labeling material within the cell.

In another embodiment, viable labeled eucaryotic cells, labeled using the process set forth above, are used for the diagnostic imaging of pathological sites in a patient. This embodiment contains the additional steps of: (1) administering said labeled cells to a patient; and (2) monitoring the localization of the label in the patient to image the locus of a specific pathosis.

In one embodiment, after the electrically-induced cell membrane pores are allowed to reseal, the first type cells are removed from the suspension and washed, preferably twice with 5 ml of platelet-free plasma. The cells are then resuspended in platelet-free plasma and the suspension is administered to the subject animal. In one embodiment, the labeled cell suspension is administered to the subject animal by injection. For example, the labeled cell suspension is drawn into a hypodermic syringe, preferably through an 18 gauge hypodermic needle, and administered to the subject animal via an injection. More preferably, the injection is administered intraperitoneally, intaarterially or intrathecally. Most preferably, the injection is administered intravenously. After administration of the labeled cells, the animal is imaged to determine the localization of the labeling agent within the subject animal. Methods of radionuclide body imaging of various types are well-known to those skilled in the art. In one embodiment the subject animal is a rabbit. In the most preferred embodiment the subject animal is a human since human health care is an ultimate object of the present invention.

In one embodiment, first type cells which demonstrate a chemotactic affinity for specific loci within the organism are labeled, administered, and the localization in an animal imaged. In another embodiment, first type cells which are significantly involved in the immune response of the organism are labeled, administered, and likewise imaged. These first type cells may be interferon-stimulated killer T-cell lymphocytes employed to image neoplasms, or helper T-cell lymphocytes employed to image autoimmune-disease tissue. In another embodiment, said first type cells may be eosinophils employed for the imaging of parasites. In yet another embodiment, said first type cells may be platelets employed to image emboli. In still another embodiment, said first type cells may be leukocytes employed to image localized absesses. In all the above embodiments, said first type cells demonstrate a chemotactic affinity for a specific pathosis and thus aggregate at that locus.

The time for imaging is highly variable, and is dependent on the labeling material used. Preferably, the animal is imaged at no less than about 15 minutes and no more than about 24 hours. However, the present invention is not limited to these imaging times because some imaging agents such as $^{95m}$Tc require observation periods of days rather than hours. The imaging technique utilized in the present invention is dependent on the labeling agent utilized and the imaging equipment available to the practitioner. Imaging techniques which may be utilized include single proton emission tomography, positron emission tomography, magnetic resonance imaging, standard x-ray imaging, computerized axial tomography, and standard gamma-ray camera imaging.

The following examples are presented to describe preferred embodiments and utilities of the present invention and are not meant to limit the present invention unless otherwise stated in the claims appended hereto.

EXAMPLE 1

General Method for Labeling Leukocytes by Electroporation in Plasma with $^{99m}$Tc-Glucoheptonate 1. A sample of blood should first be obtained, e.g., from a blood bank or from a patient using standard venipuncture technique. Preferably, 40-60 ml of whole blood should be collected in a syringe containing the anticoagulant, acid citrate dextrose formula A. 1.6 ml of acid citrate dextrose formula A is added for every 10 ml of whole blood collected. To facilitate the separation of cell types hydroxyethyl starch is added to the syringe. 3 ml of hydroxyethyl starch is added for every one ml of whole blood collected.

2. The leukocytes are then separated from the whole blood, e.g., by sedimentation and centrifugation. A preferred procedure for separating leukocytes is to invert the syringe and gently mix the whole blood. The syringe should then be placed at 45° angle with the needle superior to the rest of the syringe. This syringe should not be disturbed for about 30-60 minutes to allow the red blood cells to sediment. The leukocyte-rich plasma supernatant is then removed and centrifuged at 225 x g for five minutes. This will pellet the leukocytes.

3. The leukocytes are then placed in a non-toxic electrically conductive media, e.g., platelet-free plasma. A preferred procedure for obtaining platelet-free plasma is to first obtain whole blood as set forth in step 1. Then centrifuge the whole blood at 800 x g for 20 minutes. The cells and platelets will form a pellet, this should be discarded. The supernatant platelet-free plasma should be saved. The leukocyte-pellet of step 2 is then gently suspended in the platelet-free plasma. Preferably, a 30% suspension of cells in plasma is created.

4. A labeling material is then added to the media (leukocyte suspension), e.g., $^{99m}$Tc-glucoheptonate. Although, a number of different labeling materials may be used for labeling with electroporation, $^{99m}$Tc-glucoheptonate is used by way of example. To the leukocyte suspension add $^{99m}$Tc-glucoheptonate in saline in a ratio of four parts leukocyte suspension to one part $^{99m}$glucoheptonate in saline.

5. The media should then be pulsed for a period of time with an electric field. This field should be sufficient to render the membranes of the leukocytes permeable. The $^{99m}$Tc-glucoheptonate should then enter the leukocyte. The $^{99m}$Tc-glucoheptonate will then become trapped within the leukocyte upon cessation of the pulsing.

A preferable procedure to accomplish this is to place 0.8 ml of the leukocyte/$^{99m}$gluocoheptonate suspension in an electroporation cuvette. Then place this cuvette in a 4° C. ice water bath for 10 minutes. Then remove the cuvette and place it in a electroporation chamber. The pulse length and field strength parameters on the electroporation apparatus are set. Successful field strength ranges for labeling include 2.0 kilovolts/cm to 5.0 kilovolts/cm and pulse lengths range from 30 microseconds to 2 milliseconds. The electroporation chamber is discharged from 1 to 20 times depending on the pulse length and field strength parameters previously set. The leukocyte/$^{99m}$Tc-glucoheptonate suspension is then removed from the electroporation apparatus and placed in a 4° C. ice bath for 10 to 60 minutes. The leukocyte/$^{99m}$Tc-glucoheptonate suspension is then transferred to a new tube and placed at room temperature for 10 minutes. The leukocyte/$^{99m}$Tc-glucoheptonate suspension is then placed in a 37° C. water bath for 30 to 60 minutes. This should allow for the resealing of the cell membrane pores. A plurality of the leukocytes should now be labeled with $^{99m}$Tc-glucoheptonate. The cells should be washed twice with 5 ml platelet-free plasma to remove the $^{99m}$Tc-glucoheptonate not incorporated into the leukocytes.

6. The washed labeled cells are then administered to a patient. A preferred procedure for administering the labeled cells to a patient is to first count the radioactivity of the leukocyte/$^{99m}$Tc-glucoheptonate suspension in a dose calibrator, record the value and the percentage of cells labeled is calculated. The washed cells are resuspended in 5 ml of plasma. The suspension is drawn into a 5 ml syringe for injection into a patient, preferably intravenously.

7. The localization of the labeled cells in the patient is monitored to image the locus of a specific pathosis. The patient may be imaged from one hour to 48 hours. However, by way of example, leukocytes labeled with $^{99m}$Tc-glucoheptonate can be imaged at 4 hours and 18 hours.

EXAMPLE 2

Labeling leukocytes by electroporation in plasma with $^{99m}$Tc-glucoheptonate (trial one)

1. 60 ml of blood was collected from a blood bank. The blood was collected in a syringe containing the anticoagulant acid citrate dextrose formula A. The syringe contained 1.6 ml of acid citrate dextrose formula for every 10 ml of whole blood. The facilitate the separation of cell types, hydroxyethyl starch was added to the syringe. 3 ml of hydroxyethyl starch was added for every 10 ml of whole blood.

2. The leukocytes were separated from the whole blood collected in step 1. To separate the leukocytes from the whole blood the syringe was inverted and the whole blood was gently mixed. The syringe was then placed at a 45° angle with the needle superior to the rest of the syringe. The syringe was not disturbed for 30–60 minutes to allow the red blood cells to sediment. The leukocyte-rich plasma supernatant was removed from the syringe and placed in a 50 ml polypropylene tube. This tube was centrifuged at 225 x g for five minutes to pellet the leukocytes.

3. The separated leukocytes were then placed in a non-toxic, electrically conductive media. Platelet-free plasma was obtained by first collecting 20 ml of whole blood as generally set forth in step 1. This blood was centrifuged at 800 x g for 20 minutes. The cells and platelets formed a pellet and were discarded. The platelet-free plasma supernatant was saved. The leukocyte pellet of step 2 was gently suspended in platelet-free plasma in order to make a 30% suspension of cells in plasma. The leukocyte suspension was divided into two equal volumes. One volume of the leukocyte suspension was used as a control. These volumes of leukocyte suspension were treated identically except that the control was never electroporated.

4. The labeling material, $^{99m}$Tc-glucoheptonate, was added to both leukocyte suspensions. $^{99m}$Tc-Glucoheptonate in saline was added to the leukocyte suspensions in a ratio of four parts leukocyte suspension to one part $^{99m}$Tc-glucoheptonate in saline.

5. The non-control leukocyte suspension was then pulsed for a period of time with an electric field. The field was sufficient to render the cell membranes of the leukocytes permeable so that the $^{99m}$Tc-glucoheptonate could permeate the cells. The $^{99m}$Tc-glucoheptonate became trapped within the leukocyte upon the cessation of the pulsing. This produced labeled cells.

Specifically, 0.8 ml of the non-control leukocyte/$^{99m}$Tc-glucoheptonate suspension was placed in a electroporation cuvette (# 58-017-847, VWR scientific, Houston, TX). This cuvette was placed in 4° C. ice bath for 10 minutes. The cuvette was then removed and placed in the electroporation chamber (0.35 cm gap, 0.8 ml volume, transfector 100, BTX, San Diego, CA). The pulse length was set at 0.03 milliseconds and the field strength at 3.75 kilovolts/cm on the electroporation apparatus. The electroporation chamber was discharged three times. The cuvette was removed from the electroporation device and return to the 4° C. ice water bath for 10–60 minutes. The leukocyte/$^{99m}$Tc-glucoheptonate suspension was then transferred to a 5 ml polypropylene tube at room temperature for 10 minutes. The leukocyte/$^{99m}$Tc-glucoheptonate suspension was then transferred to a 37° water bath for 30–60 minutes. This allowed for the resealing of the cell membrane pores. The control leukocyte/$^{99m}$Tc-glucoheptonate suspension was also placed in the different water baths for identical time periods.

6. The leukocyte/$^{99m}$Tc-glucoheptonate suspensions were removed from the 37° C. water bath of step 5 and the radioactivity of the suspensions was counted in a dose calibrator and the values were recorded. The leukocytes of each suspension were then washed twice with 5 ml of (platelet-free plasma to remove any 99mTc-glucoheptonate not incorporated into the leukocytes. The radioactivity for both the groups of washed leukocytes was determined in the dose calibrator. These values were recorded and the percentage of leukocytes labeled with $^{99m}$Tc-glucoheptonate was calculated for both the control and the non-control (electroporated) leukocytes.

| Results | |
|---|---|
| Radioisotope | 99mTc-Glucoheptonate |
| Cell Type | Leukocytes |
| Kilovolts Per Centimeter | 3.75 kv/cm |
| Pulse Length | 0.03 msec |
| Number of Pulses | 3 |
| Pulsed Cells Labeled | 3.6% |
| Control Cells Labeled | 0% |
| Viability of Leukocytes* | 87% |

*Trypan blue viability study

EXAMPLE 3

Labeling leukocytes by electroporation in plasma with $^{99m}$Tc-glucoheptonate (trial two)

(a) Example 3 followed the experimental protocol of Example 2.

| Results | |
|---|---|
| Radioisotope | 99mTc-Glucoheptonate |
| Cell Type | Leukocytes |
| Kilovolts Per Centimeter | 3.75 kv/cm |
| Pulse Length | 0.03 msec |
| Number of Pulses | 3 |
| Pulsed Cells Labeled | 3.3% |
| Control Cells Labeled | .64% |
| Viability of Leukocytes* | 90% |

*Trypan blue viability study

EXAMPLE 4

Labeling of leukocytes by electroporation in plasma using $^{99m}$Tc-methylene diphosphonate (a) Example 4 follows the experimental protocol of Example 2 with the following exceptions. $^{99m}$Tc-methylene diphosphonate was substituted for $^{99m}$Tc-glucoheptonate as the labeling agent in step 4. The pulse length was set at 0.50 milliseconds in step 5. The field strength was set at 3.10 kilovolts/cm in step 5. The number of pulses was 10 in step 5.

| Results | |
|---|---|
| Radioisotope | 99mTc-MDP |
| Cell Type | Leukocytes |
| Kilovolts Per Centimeter | 3.10 kv/cm |
| Pulse Length | 0.50 msec |
| Number of Pulses | 10 |
| Pulsed Cells Labeled | 4.1% |
| Control Cells Labeled | .7% |
| Viability of Leukocytes* | 85% |

*Trypan blue viability study

EXAMPLE 5

Labeling leukocytes by electroporation in plasma using $^{67}$gallium citrate (a) Example 4 followed the experimental procedure of example 2 with the following exceptions. $^{67}$Gallium citrate was substituted as the labeling agent for $^{99m}$Tc-glucoheptonate in step 4. Pulse length was set at 0.50 milliseconds in step 5. Field strength was set at 3.00 kilovolts/cm in step 5. The number of pulses was 10 in step 5.

| Results | |
|---|---|
| Radioisotope | 67-Gallium Citrate |
| Cell Type | Leukocytes |
| Kilovolts Per Centimeter | 3.00 kv/cm |
| Pulse Length | 0.50 msec |
| Number of Pulses | 10 |
| Pulsed Cells Labeled | 3.1% |
| Control Cells Labeled | 0% |
| Viability of Leukocytes* | 80% |

*Trypan blue viability study

EXAMPLE 6

Labeling leukocytes by electroporation in plasma using $^{99m}$Tc-pyrophosphate (a) The process of this example followed the experimental procedure of example 2 with the following exceptions. $^{99m}$Tc-pyrophosphate was substitute for $^{99m}$Tc-glucoheptonate as the labeling agent in step 4. The pulse length was set at 2.39 milliseconds in step 5. The field strength was set at 2.00 kilovolts/cm in step 5. The number of pulses was 1 in step 5.

| Results | |
|---|---|
| Radioisotype | 99mTc-Pyrophosphonate |
| Cell Type | Leukocytes |
| Kilovolts Per Centimeter | 2.00 kv/cm |
| Pulse Length | 2.39 msec |
| Number of Pulses | 1 |
| Pulsed Cells Labeled | 8.7% |
| Control Cells Labeled | 1.6% |
| Viability of Leukocytes* | 91% |

*Trypan blue viability study

EXAMPLE 7

Labeling erythrocytes by electroporation in plasma using $^{99m}$Tc-methylene diphosphonate (a) Example 7 follows the experimental procedure of example 2 with following exceptions. In step 2 erythrocytes were separated by sedimentation and saved. The leukocyte pellet of step 2 was discarded. Erythrocytes were then substitute for the leukocytes of steps 3, 4, 5, and 6. $^{99m}$Tc-methylene diphosphonate was substituted for $^{99m}$Tc-glucoheptonate as the labeling agent in step 4. The pulse length was 2.39 milliseconds in step 5. The field strength was 2.00 kilovolts/cm in step 5. The number of pulses was one.

| Results | |
|---|---|
| Radioisotope | 99mTc-MDP |
| Cell Type | Erythrocytes |
| Kilovolts Per Centimeter | 3.10 kv/cm |
| Pulse Length | 0.03 msec |
| Number of Pulses | 3 |
| Pulsed Cells Labeled | 5.2% |
| Control Cells Labeled | .6% |
| Viability of Leukocytes* | 88% |

*Trypan blue viability study

EXAMPLE 8

General method for labeling platelets by using electroporation in plasma

1. A sample of blood should first be obtained, e.g. from a blood bank or from a patient with an 18 gauge needle, using standard venipuncture technique. Preferably, 40–60 ml of whole blood is collected in a syringe containing the anticoagulant acid citrate dextrose formula A. 1 .6 ml of acid citrate dextrose formula A is added for every 10 ml of whole blood collected.

2. The platelets should then be separated from the whole blood collected. Plastic pipettes and plastic tubes will be used for pipetting and centrifuging in this procedure. A preferred procedure for separating the platelets from the whole blood is to first transfer the whole blood from the syringe to ten separate 10 ml polypropylene tubes. Then centrifuge the tubes at 150 x g for 20 minutes. This will create platelet-rich plasma supernatant. Remove the supernatant plasma and place in six 10 ml polypropylene tubes and centrifuge at 800 x g for 10 minutes. This will pellet the platelets. Remove the platelet-free plasma supernatant and store at 37° C. for later use.

3. The platelets will then be introduced into a non-toxic electrically conductive media, e.g., platelet-free plasma. Preferably, the platelet pellets is placed in the platelet-free plasma from step 2 and gently suspended to make suspension of platelets in plasma. Combine the platelet suspensions from the six tubes into one polypropylene 5 ml tube.

4. A labeling agent is then added to the platelet suspension. Although numerous labeling agents may be successfully used with the inventive method, $^{99m}$Tc-pyrophosphate will be used by way of example. To the platelet suspension add $^{99m}$Tc-pyrophosphate in saline in a ratio of 4 parts leukocyte suspension to 1 part $^{99m}$Tc-pyrophosphate in saline.

5. The platelet/$^{99m}$Tc-pyrophosphate suspension should then be pulsed for a period of time with an electric field. This electric field will cause the cell membranes of the platelet to become permeable. The $^{99m}$Tc-pyrophosphate will then permeate the platelets. Upon cessation of the electric field the $^{99m}$Tc-pyrophosphate will become trapped within the platelets to produce labeled platelets. A preferred procedure to accomplish this is to first add 0.8 ml of the platelet/$^{99m}$Tc-pyrophosphate suspension to an electroporation cuvette (#358-017-847, VWR Scientific, Houston, TX). This cuvette is then placed in a 4° C. ice water bath for 10 minutes. The cuvette is then removed and placed it in the electroporation chamber (0.35 cm gap, 0.8 ml volume, Transfector 100, BTX, San Diego, CA). The pulse length and field strength parameters on the electroporation apparatus should be set. Field strength ranges for labeling will include 2.0 kilovolts/cm to 5.0 kilovolts and pulse length ranges will include 2.0 milliseconds to 4.0 milliseconds. The electroporation chamber should be pulsed from one time to 10 times. After cessation of the electric field, the platelet/$^{99m}$Tc-pyrophosphate suspension should be removed from the electroporation apparatus and returned to the ice water bath for 10-60 minutes. The platelet/$^{99m}$Tc-pyrophosphate suspension in the tube should then be transferred to a 37° C. water bath for 30-60 minutes. This should allow for the resealing of the cell membrane pores. A plurality of platelets should now be labeled with $^{99m}$Tc-pyrophosphate.

6. The percentage of cells labeled is then calculated. The suspension is removed from the 37° C. water bath of step 5 and the radioactivity is counted in a dose calibrator and the value recorded. The platelets are then washed twice with 5 ml of platelet-free plasma to remove any $^{99m}$Tc-pyrophosphate not incorporated in the platelets. The radioactivity of the washed cells is then counted in the dose calibrator. This value is recorded and the percentage of cells labeled is calculated.

7. The labeled platelets are then administered to a patient. The labeled washed platelets should be suspended in 5 ml of plasma and drawn into a 5 ml syringe for injection. The platelet suspension is then injected into the patient. Preferably, the labeled platelets are injected intravenously.

8. The localization of the label in the labeled platelet is then monitored to image the locus of a specific pathosis. The patient may be imaged from one hour to 48 hours. However, by way of example, platelets labeled with $^{99m}$Tc-pyrophosphate can be imaged at 4 and 18 hours.

EXAMPLE 9

Labeling platelets by using electroporation in plasma

1. A sample of blood was obtained from a blood bank. 40-60 ml of whole blood was collected in a syringe containing the anticoagulant acid citrate dextrose Formula A. 1.6 ml of acid citrate dextrose Formula A was added for every 10 ml of whole blood collected.

2. The platelets were separated from the whole blood. Plastic pipettes and plastic tubes were used for pipetting and centrifuging in this procedure. The whole blood collected in step 1 was transferred from the syringe to ten separate 10 ml polypropylene tubes. These tubes were then centrifuged at 15 x g for 20 minutes to create platelet-rich plasma in the supernatant. The supernatant plasma was removed and placed into six 10 ml polypropylene tubes and centrifuged at 800 x g for 10 minutes to pellet the platelets. The platelet-free plasma supernatant was removed and stored at 37° C. for later use.

3. The platelets were then introduced into a non-toxic electrically conductive media, e.g., platelet-free plasma. The platelet pellets from step 2 were gently suspended in the platelet-free plasma from step 2 to make a suspension of platelets in plasma the concentration of 200 K/microliter. The platelet suspensions from the six tubes were combined into one polypropylene 5 ml tube.

4. A labeling agent was then added to the platelet suspension, e.g., $^{99m}$Tc-pyrophosphate. $^{99m}$Tc-pyrophosphate in saline was added to the platelet suspension in a ratio of 4 parts leukocyte suspension to 1 part $^{99m}$Tc-pyrophosphate n saline. The platelet/$^{99m}$Tc-pyrophosphate suspension was then divided equally into two samples. One sample became the control sample which was not electroporated, and one sample became the non-control sample which was electroporated. Otherwise both the control and non-control sample were treated identically.

5. The non-control platelet/$^{99m}$Tc-pyrophosphate suspension was pulsed with a electric field. 0.8 ml of the platelet/$^{99m}$Tc-pyrophosphate suspension was added to an electroporation cuvette (#358-017-847, VWR Scientific, Houston, TX). This cuvette was placed in a 4° C. ice water bath for 10 minutes. The cuvette was then removed and placed it in the electroporation chamber (0.35 cm gap, 0.8 ml volume, Transfector 100, BTX, San Diego, CA). The pulse length and field strength parameters on the electroporation apparatus were set. The field strength was set at 2.1 kilovolts/cm and the pulse length was set at 2.4 milliseconds. The electroporation chamber was pulsed one time. After cessation of the electric field the platelet/$^{99m}$Tc-pyrophosphate suspension was removed from the electroporation apparatus and returned to the ice water bath for 10-60 minutes. The platelet/$^{99m}$Tc-pyrophosphate suspension in the tube was then transferred to a 37° C. water bath for 30-60 minutes. This allowed for the resealing of the cell membrane pores. A plurality of platelets were labeled with $^{99m}$Tc-pyrophosphate.

6. The percentage of cells labeled in the control and non-control samples was calculated. The suspensions were removed from the 37° C. water baths of step 5 and their radioactivity was counted in a dose calibrator and the values were recorded. The platelets were then washed twice with 5 ml of platelet-free plasma to remove $^{99m}$Tc-pyrophosphate not incorporated into the platelets. The radioactivity of the washed cells was then counted in the dose calibrator. The values were recorded and the percentage of cells labeled was calculated for both the control and non-control samplers.

7. A standard platelet agglutination study was then done in order to determine the viability of both control and non-control (labeled cells) cells. The platelet agglutination curves demonstrated normal platelet activity in response to bovine thombin, indicating good platelet viability for both the control and non-control cells (labeled).

The electroporated platelets prepared by this procedure demonstrated 250% greater percent label of $^{99m}$Tc-pyrophosphate than the control platelets. Also, the electroporated platelets demonstrated no adverse affects from the labeling procedure.

Changes may be made in the construction, operation and arrangement of the various cells, labels, steps and procedures described herein without departing from the concept and scope of the invention as defined in the following claims.

I claim:

1. A process for diagnostically imaging pathological sites, the process comprising the steps of:
   (a) collecting an amount of living cells;
   (b) separating from said amount a plurality of first type cells,
   (c) introducing a quantity of said first-type cells into a non-toxic media, said media being electrically conductive;
   (d) introducing a labeling material which is x-ray opaque, gamma particle emitting, paramagnetic, proton emitting or positron emitting into said media;

(e) pulsing said media for a period of time with an electric field sufficient to render membranes of said first type cells permeable so that said labeling material permeates the cells and becomes trapped therein upon cessation of the pulsing to produce labeled cells;

(f) administering said labeled cells to a patient; and (g) monitoring localization of label in said labeled cells in the patient to image the locus of a specific pathosis.

2. The process of claim 1 wherein said first type cells are selected from the group consisting of: leukocytes, erythrocytes, T-cell lymphocytes, eosinophils and platelets.

3. The process of claim 1 wherein said first type cells demonstrate a chemotactic affinity for specific loci within the patient.

4. The process of claim 1 wherein said first type cells are of a type involved in immune responses.

5. The process of claim 1, wherein said first type cells demonstrate a chemotactic affinity to aggregate at a specific pathosis.

6. The process of claim 1 wherein said media is a suspension.

7. The process of claim 1 wherein said electric field is generated by an electroporation device.

8. The process of claim 1 wherein said media is normal saline solution.

9. The process of claim 1 wherein said media is platelet-free plasma.

10. The process of claim 1 wherein said labeling material comprises $^{99m}Tc$, $^{95m}Tc$, $^{123}I$ or $^{67}Ga$.

11. The process of claim 1 wherein said amount of living cells is collected from blood of a patient to be administered labeled cells.

12. The process of claim 1 wherein monitoring localization of the label involves single photon emission tomography.

13. The process of claim 1 wherein monitoring localization of label involves positron emission tomography.

14. The process of claim 1 wherein monitoring localization of label involves magnetic resonance imaging.

15. The process of claim 1 wherein monitoring localization of label involves standard x-ray imaging.

16. The process of claim 1 wherein administering of said labeled cells is done by intravenous injection.

17. The process of claim 1 wherein administering of said labeled cells is done by intrathecal injection.

18. The process of claim 1 wherein administering of said labeled cells is done by intraperitoneal injection.

19. The process of claim 1 wherein administering of said labeled cells is done by intraarterial injection.

20. The process of claim 1 wherein said living cells are human cells.

21. The process of claim 1 wherein said labeling material of step (d) is introduced into said media prior to the introduction of said first type cells.

22. The process of claim 1 wherein said labeled cells of step (e) are removed from said media and placed in a media suitable for administration to a patient prior to administering said labeled cells to a patient.

23. The process of claim 1 wherein said first type cells are interferon-stimulated killer T-cell lymphocytes.

24. The process of claim 23 wherein the killer T-cell lymphocytes are employed to image neoplasms.

25. The process of claim 1 wherein said first type cells are helper T-cell lymphocytes.

26. The process of claim 25 wherein the helper T-cell lymphocytes are employed to image autoimmune-disease tissue.

27. The process of claim 1 wherein said first type cells are eosinophils.

28. The process of claim 27 wherein the eosinophils are employed for imaging of parasites.

29. The process of claim 1 wherein said first type cells are platelets.

30. The process of claim 29 wherein the platelets are employed to image emboli.

31. The process of claim 1 wherein said first type cells are leukocytes.

32. The process of claim 31 wherein the leukocytes are employed to image localized occult absesses.

33. The process of claim 1 wherein said first type cells are erythrocytes.

34. The process of claim 33 wherein the erythrocytes are employed to image internal hemorrhages.

35. The process of claim 1 wherein said labeling material is a radiopharmaceutical.

36. The method of claim 35 wherein the radiopharmaceutical is selected from the group consisting of: $^{99m}Tc$-glucoheptonate, $^{99m}Tc$-methylene diphosphonate, $^{99m}Tc$-pyrophosphate, and $^{67}$ gallium citrate.

37. The process of claim 1 wherein said labeling material is a stable paramagnetic isotope.

38. The process of claim 37 wherein said labeling material is gadolinium.

39. The process of claim 1 wherein monitoring localization of label involves computerized axial tomography.

40. The process of claim 39 wherein said labeled cells are administered to an animal and the localization of said cells is monitored to image the locus of a specific pathosis.

* * * * *